United States Patent [19]

Jakstys et al.

[11] 4,228,236

[45] Oct. 14, 1980

[54] PROCESS OF PRODUCING CARCINOEMBRYONIC ANTIGEN

[75] Inventors: Milda M. Jakstys, Chicago, Ill.; Baldwin H. Tom; Barry D. Kahan, both of Houston, Tex.

[73] Assignee: Northwestern University, Evanston, Ill.

[21] Appl. No.: 906,036

[22] Filed: May 15, 1978

Related U.S. Application Data

[63] Continuation of Ser. No. 785,565, Apr. 7, 1977, abandoned.

[51] Int. Cl.² ............................................. C12K 9/00
[52] U.S. Cl. .................................... 435/1; 424/12
[58] Field of Search ................................. 195/1.8

[56] References Cited

U.S. PATENT DOCUMENTS 4,017,361  4/1977  Febvre ........................... 195/1.8

Primary Examiner—V. D. Turner
Attorney, Agent, or Firm—Tilton, Fallon, Lungmus & Chestnut

[57] ABSTRACT

Carcinoembryonic antigen (CEA) is produced in vitro from the cell lines LS-180 (ATCC No. CL-187), LS-174T (ATCC No. CL-188), and cells derived therefrom. The CEA thus produced can be used as a standard source for radioimmunoassay procedures to determine CEA plasma levels.

5 Claims, No Drawings

PROCESS OF PRODUCING CARCINOEMBRYONIC ANTIGEN

The invention described herein was made in the course of work under a grant from the Department of Health, Education, and Welfare.

CROSS-REFERENCE

This is a continuation of co-pending application Ser. No. 785,565, filed Apr. 7, 1977, now abandoned.

BACKGROUND

The carcinoembryonic antigen (CEA) was first described by Gold et al in 1965; *J. Exp. Med.*, 121, 439–462; 122, 467–487. The CEA was isolated from human colonic adenocarcinoma tissue. A radioimmunoassay for detecting CEA in patients' sera was subsequently developed by Thomson et al (1969), *Proc. Nat. Acd. Sci.* 64, 161. A similar diagnostic procedure has been commercialized by Roche Diagnostics Division of Hoffmann-LaRoche, Inc. Nutley, N.J. While such assay procedures are not presently recommended as a screen test to detect cancer, CEA titers can be used to monitor remission in colon and certain other types of cancer, and also for some nonmalignant inflammatory diseases. Most healthy non-smoking subjects have titer levels below 2.5 ng/ml. The elevated CEA titers that occur during disease states tend to return to levels below 2.5 ng/ml following successful therapy, but usually remain elevated when refractory disease is present.

In the CEA-ROCHE radioimmunoassay procedure, the antigen (CEA) is extracted from the plasma test sample and allowed to react with specific CEA antiserum. $^{125}$I-CEA is then added and allowed to react with the remaining CEA antiserum. The $^{125}$I-CEA bound to the antibody is separated from excess free $^{125}$I-CEA with zirconyl phosphate gel and the bound $^{125}$I-CEA determined by assay in a gamma scintillation spectrometer. The partition of $^{125}$I-CEA between bound and free fractions is a function of the amount of CEA present in the plasma. The amount of CEA present in the plasma sample is then determined from a standard inhibition curve.

The CEA for use as radio-labelled CEA in determining plasma levels has heretofore been obtained from human cancer tissue which has been surgically removed, particularly adenocarcinoma tissue of tumors originating in the digestive system. (See U.S. Pat. Nos. 3,663,684, 3,697,638 and 3,956,258, assigned to Hoffmann-LaRoche Inc.). The surgically derived cancer tissue is homogenized, and subjected to an extraction and purification procedure to obtain the CEA.

As far as is known, no process has heretofore been described for preparing a standardized CEA reference by in vitro culturing of CEA-producing cells. However, such a process would have many advantages. It would provide a stable source of CEA from well-characterized cells and thus be independent of human cancer tissue as a starting material. Moreover, it could be carried out on a production basis to provide a uniform and reproducible source of CEA. It is therefore of considerable importance that the present invention does provide such a process.

SUMMARY OF INVENTION

The process of the present invention utilizes CEA-producing cells which have been adapted for in vitro culture. Prior to the present invention, it had not been demonstrated that human colonic adenocarcinoma cells could be established as reproducible cell lines which would not only grow satisfactorily in vitro but also retain their ability to produce CEA in high yields. The previously established line HT-29 produces CEA in such small amounts that it would be impractical to use it for commercial production of CEA. The primary cell line used in the process of this invention LS-180 (ATCC No. CL-187) is highly productive of CEA. Other CEA-producing cell lines have been derived from LS-180, such as LS-174T (ATCC No. CL-188). In practicing the process of the invention, the CEA-producing cells are cultured in a suitable nutrient medium for growth of the cells. After the culturing has been completed, the CEA is recovered.

DETAILED DESCRIPTION

The parent cell line LS-180 (ATCC No. CL-187) was developed from surgically-derived epithelial cells of human colonic adenocarcinoma tissue. The adaptation of the cells to in vitro growth required many months. The culture medium used for the adaptation was a standard medium referred to as minimal essential medium (MEM) supplemented with 20% by volume heat-inactivated fetal bovine serum. The resulting cell culture, which is capable of serial passages has been designated as the parent cell line LS-180. The designation of the culture as a "line" conforms with the definition published by Fedoroff in the *Tissue Culture Association Manual,* Vol. 1, No. 1, pp. 53–57 (1975). This cell line has been deposited with the American Type Culture Collection under No. CL-187.

Another closely related cell line has been derived from LS-180. Cultures of LS-180 were trypsinized (0.1% trypsin in 0.02% versene, pH 7.4) to produce the cell line designated as LS-174T. The trypsinization removes the mucinous coat (probably containing mucin trapped CEA and debris) from the cells, resulting in relatively non-fuzzy colonies. To maintain this characteristic, the LS-174T cells can be re-trypsinized with each passage. Because of their relative mucin-free condition, the cells tend to grow more rapidly, although producing CEA at a somewhat reduced level from the parent cells LS-180. The cell line LS-174T has also been deposited with the American Type Culture Collection under ATCC No. CL-188.

The cells of LS-180 and LS-174T are morphologically similar, appearing as 20 to 40 μm diameter, oval or polygonal cells. Both cell cultures produce mucin CEA as well as the colon-specific antigen CSA. They can be propagated in hamster cheek pouches and in immunodeprived mice. They are not contact-inhibited and will grow into cell masses in culture.

Either LS-180 or LS-174T can be employed in practicing the present invention. Although LS-180 grows more slowly under in vitro culture conditions, it produces CEA in greater yields than trypsinized variants thereof such as LS-174T. Other cell cultures can easily be developed from these established lines. One procedure is known as cloning in which a single cell is selected, and cultured to produce a cloned cell line. Such derived clone cell lines as well as trypsinized variants thereof can also be used in practicing the present invention. In general, the cell lines should be capable of producing CEA in an amount of at least 100 nanograms (ng) of CEA per $10^6$ cells, and preferably at least 200 ng CEA/$10^6$ cells. With the lines LS-180 and LS-174T yields in the range of 400–800 ng CEA/$10^6$ cells can be obtained. The data in Table A is representative.

TABLE A

| Cells | Population Doubling (hrs) | Duration of Incubation (days) | Amount of CEA* |
|---|---|---|---|
| LS-180 | 72 | 15 | 775 |
| LS-174T | 22 | 7 | 401 |

*Average release of ng CEA/$10^6$ cells

Various culture mediums can be used in practicing the present invention which are capable of supporting the growth of the CEA-producing cells. For example, the medium may be Minimum Essential Medium (MEM) supplemented with fetal bovine serum. Minimal Essential Medium (MEM) is available commercially from Grand Island Biological Co., Grand Island, N.Y. From 10 to 20 parts by volume of fetal calf serum may be combined per 100 parts of MEM (pH 7.3) to produce an enriched culture media. The CEA-producing cells propagate well in this medium, although it should be understood that other similar media can be used.

The culturing may be carried out at a temperature in the range of 25° to 40° C. Culturing at 37° C. is optimal. No pH adjustments are made during culturing, but the medium is changed when necessary for continued growth of the cells.

The desirable duration of the culturing will depend on economic considerations. The culturing will be continued until the cell population has at least doubled, and in the preferred commercial operation, the cell population will be increased by many times, incubation times of from 7 to 15 days or longer may be needed to maximize the CEA production. The culturing may be carried out in 150 cm$^2$ tissue culture flasks, or in larger vessels, such as roller bottles.

On completion of the culturing, most of the CEA will be associated with the cells, although some CEA will be present in the culture medium. Whether or not the CEA is recovered from both the medium or the cells, or only from the cells, will depend on economic considerations. The cell mass can readily be separated from the residual liquid culture medium by centrifugation. Alternatively, the cells can be lysed by a freeze-thaw procedure, liberating the CEA into the culture medium. On separation of the lysed cell material, the CEA can be recovered from the liquid medium.

The previously established human colonic adenocarcinoma cell line, HT-29, produces CEA at much lower levels than the cell lines used in the process of the present invention. The HT-29 cell line was described by Fogh et al in *Human Tumor Cells In Vitro* (1975), Plenum Publishing Corp., New York, pp. 115–154. Using a sample of HT-29 supplied by Dr. J. Fogh, comparative data was obtained, as set out below in Table B.

TABLE B

| | Amount CEA, nanogram ($\times 10^{-9}$)/cell | | |
|---|---|---|---|
| Source | LS-180 | HT-29 | LS-180/HT-29 |
| Cell Pellet | 129,000 | 4000 | 30 |
| Culture Supernate* | 6,000 | 6.6 | 909 |

*Amount released into the culture medium per cell over 24 hrs.

After the culturing of the CEA-producing cells has been completed, and the CEA has been recovered either with the cells, or in the supernatant, or both, the CEA can be further processed. For example, the CEA can be purified by the method described by Gold et al, *J. Exp. Med.*, 122, 467 (1965), or the modified CEA isolation procedure of Coligan et al, *Immunochemistry* 9, 377 (1972). Other procedures for recovery and isolation of CEA have been described in the patent literature. See U.S. Pat. Nos. 3,663,684, 3,697,638 and 3,956,258. Although these procedures refer to the preparation of CEA from surgically-derived colon cancer tissue, they can also be used for the recovery of CEA from the cell cultures of this invention. The cells, culture medium, or both may be extracted with a glycoprotein solvent, such as perchloric acid, which will extract the CEA. The extract may be further purified by dialysis against water or polyethyleneglycol (see U.S. Pat. No. 3,956,258), and further purified by chromatography. The term "CEA" as used in this application is intended to refer collectively to the active carcinoembryonic antigens, including the antigen fractions referred to as components A and B. The characteristics of these components and a means for separating them, if desired, is described in U.S. Pat. No. 3,697,638.

The process of this invention is further illustrated by the following specific examples.

EXAMPLE I

Culture of LS-180 Cell Monolayers in Flasks

Stock LS-180 cells are subcultured by detachment of cell monolayers with a rubber policeman. The loosened cells are decanted into a sterile conical centrifuge tube and collected by centrifugation at 270$\times$g for 10 minutes at ambient temperature. The resultant pellet is resuspended in 2/3 volume fresh MEM20 (MEM with Hank's salts, L-glutamine, non-essential amino acids, 100 units of pencillin/ml, 50 $\mu$g of streptomycin/ml, and sodium bicarbonate to bring pH to 7.3 plus 20% fetal bovine serum) with 1/3 volume spent "conditioned" media and cultured in a 25, 75, or 150 cm$^2$ plastic tissue culture flask, depending on the amount of cells in the suspension. In the usual passage, a 1:2 split is made, that is, from one flask, two new flasks of the same size as prepared. From a 1:2 split, LS-180 cells will become a confluent monolayer in 3—4 weeks. If not subcultured, the LS-180 cells will continue to grow, forming multi-layer colonies. The flasks are incubated at 37° C. in 5% $CO_2$ with humidified air. The cultures are refed with 2/3 fresh MEM20 as needed. CEA can be harvested from the spent supernatant culture media and from the cells (see Tables A & B). The spent media is simply decanted from the flask and processed for CEA. The cells are collected by mechanical scraping, frozen-thawed five times and then processed for CEA by the perchloric acid method described by Gold et al, *J. Exp. Med.*, 122, 465 (1965), or the modified procedure of Coligan et al, *Immunochemistry*, 9, 377 (1972).

EXAMPLE II

Culture of LS-174T Cell Monolayer in Flasks

Stock LS-174T cells are subcultured by trypsinization with 0.1% trypsin in 0.02% ethylenediaminetetraacetic acid (EDTA), pH 7.3. For passage, a 1:2 or 1:3 split is made from each flask. A 1:2 split of LS-174T cells will grow to a confluent monolayer in 4–5 days. Detached cells are collected in MEM20 by centrifugation (270$\times$g, 10 minutes) and seeded into flask using 2/3 fresh MEM20. CEA is extracted from the LS-174T cells and culture media as in Example I.

EXAMPLE III

Culture of LS-174T Cell Monolayers and Cell Suspension in Roller Bottles

Stock LS-174T cells collected by trypsinization are seeded into plastic tissue culture roller bottles (500 ml volume) and cultured on a horizontal apparatus at 10–15 revolutions per hour in an environment of 5% $CO_2$, 95% air at 37° C. The cultures are refed at regular intervals. Cells cultured in this fashion produced abundant CEA and grew to high densities, up to 8-fold the number of cells per volume of media when compared to stationary monolayer cultures. Large clusters of LS-174T cells grew suspended in the media and were shown histologically to consist of viable cells held together by mucinous material. CEA is recovered from the cultured cells by the procedures of Example I.

Procedures are available for determining CEA levels. The assay methods of Egan et al may be used. See *J. Natl. Cancer Inst.*, 49: 887–889. More specifically, the CEA content of the sera and supernatant fluids from the cultured LS-180 or LS-174T cells are detectable by a solid phase radioimmunoassay. Anderson et al, *Immunochemistry* 12: 577–580, 1975. Perchloric acid extracts of the samples are incubated overnight at 37° C. in polystyrene tubes coated with monospecific guinea pig anti-human CEA immunoglobulin-G derived from immune sera as described by Tomata et al, *Immunology* 26: 291–298, 1974. The tubes are then rinsed in 0.01 M tris-saline buffer, pH 7, $^{125}$I-CEA is added for a 5-hr incubation, rinsed again, and counted in an automatic gamma counter. The results are directly comparable to the $^{125}$I-CEA standard in the Hoffmann-LaRoche CEA Kit (Roche Diagnostic's, Nutley, N.J.), and employed in the Z-gel method of Hansen and co-workers Hansen et al, *Human Pathol.* 5: 139–147, 1974.

We claim:

1. The process of producing carcinoembryonic antigen (CEA) in vitro, comprising culturing cells selected from the cell lines consisting of LS-180 (ATCC No. CL-187), LS-174T (ATCC No. CL-188), and CEA-producing cells derived therefrom, in a nutrient medium capable of supporting the growth of said cells until the number of cells present have at least doubled, and recovering the CEA thus produced.

2. The process of claim 1 in which said cells are from the cell line LS-180 (ATCC No. CL-187).

3. The process of claim 1 in which said cells are from the cell line LS-174T (ATCC No. CL-188).

4. The process of claim 1 in which said cells are a trypsinized form of the cell line LS-180 (ATCC No. CL-187).

5. The process of claim 1 in which said cells are cloned cells derived from the cell line LS-180 (ATCC No. CL-187).

* * * * *